United States Patent [19]

Ahlfors et al.

[11] Patent Number: 4,694,099
[45] Date of Patent: Sep. 15, 1987

[54] PROCEDURE FOR PRODUCING STEARYL-β-(3,5-DIBUTYL-4-HYDROXYPHENYL) PROPIONATE AND BIS-(β(3,5-DIBUTYL-4-HYDROXYBENZYL)-METHYLCARBOXYETHYL)SULPHIDE

[75] Inventors: Matts Ahlfors, Espoo; Salme Koskimies, Helsinki; Leila Lahtinen, Helsinki; Peter Idelman, Helsinki, all of Finland

[73] Assignee: Neste Oy, Finland

[21] Appl. No.: 841,518

[22] PCT Filed: Jun. 28, 1985

[86] PCT No.: PCT/FI85/00063
§ 371 Date: Feb. 20, 1986
§ 102(e) Date: Feb. 20, 1986

[87] PCT Pub. No.: WO86/00301
PCT Pub. Date: Jan. 16, 1986

[30] Foreign Application Priority Data

Jun. 28, 1984 [FI] Finland .................................. 842618

[51] Int. Cl.⁴ .............................................. C07C 67/03
[52] U.S. Cl. ........................................ 560/75; 560/61; 562/478
[58] Field of Search .................... 560/61, 75; 562/478; 502/152

[56] References Cited

U.S. PATENT DOCUMENTS 4,228,297 10/1980 Haeberli et al. ..................... 560/75
4,376,866 3/1983 Englaender et al. ................. 560/60

FOREIGN PATENT DOCUMENTS 0017614 10/1980 European Pat. Off. .
0102920 3/1984 European Pat. Off. .
2240609 2/1974 Fed. Rep. of Germany .

OTHER PUBLICATIONS

Kirk–Otmer Encyclopedia of Chemical Technology, Third Edition, vol. 23, pp. 179–181 and 225.

*Primary Examiner*—Werren B. Lone
*Assistant Examiner*—Vera C. Clarke
*Attorney, Agent, or Firm*—Steinberg & Raskin

[57] ABSTRACT

A procedure for producing stearyl-β-(3,5-dibutyl-4-hydroxyphenyl)propionate and bis-(β-(3,5-dibutyl-4-hydroxybenzyl)-methylcarboxyethyl)sulphide. In the procedure, a titanate-catalysis exchange esterification reaction is carried out with propionic acid ester conforming to formula (IV) and stearyl alcohol or thiodiglycol.

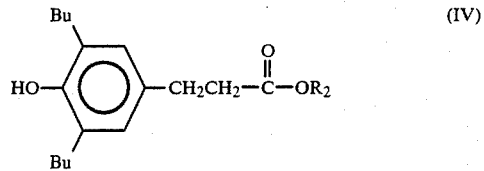

where Bu is an n-butyl, secondary butyl, isobutyl or tertiary butyl group and $R_2$ is a methyl, ethyl, propyl or butyl group.

12 Claims, No Drawings

PROCEDURE FOR PRODUCING STEARYL-β-(3,5-DIBUTYL-4-HYDROXYPHENYL) PROPIONATE AND BIS-(β(3,5-DIBUTYL-4-HYDROXYBENZYL)-METHYLCARBOXYETHYL)SULPHIDE

BACKGROUND OF THE INVENTION

The present invention concerns a procedure for producing stearyl-β-(3,5-dibutyl-4-hydroxyphenyl)propionate (I) and bis-(β(3,5-dibutyl-4-hydroxybenzyl)-methyl-carboxyethyl)-sulphide (II). Said products conform chemically to formulate I and II below and they are used mainly for stabilizing substances in rubbers and plastics.

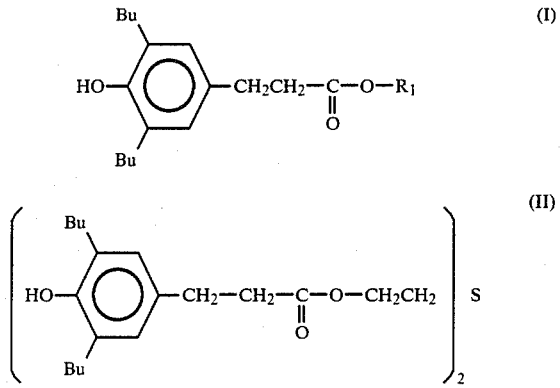

Bu = n-butyl, secondary butyl, isobutyl or tertiary butyl group
$R_1$ = stearyl group ($C_{18}H_{35}$—)

It is known in the art that these compounds can be produced in a two-step synthesis comprising (A) the addition reaction between alkylacrylate (III) and 2,6-dibutylphenol, and exchange esterification (B) of the product obtained (IV).

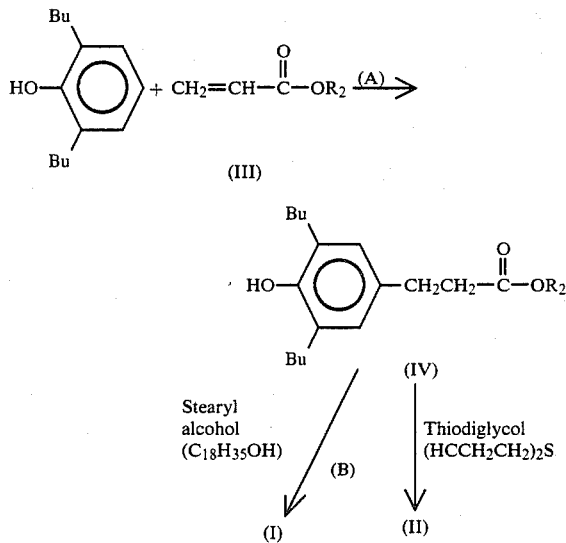

Bu = n-butyl, i-butyl, secondary butyl or tertiary butyl group
$R_2$ = methyl, ethyl, propyl or butyl group In the procedures of prior art, step (A) is usually carried out in the presence of alkali catalysts, either as a molten state reaction or using a solvent for fluid. The exchange esterification step (B), again, has been performed in the procedures of prior art using either alkaline or acid catalysts.

SUMMARY OF THE INVENTION

The procedure of the invention differs from procedures of prior art particularly in that the exchange esterification step is carried out using esters of titanic acid for a catalyst. Morever, an advantage of the procedure of the invention is that when said catalysts are used the exchange esterification reaction is substantially faster, and thus the reaction time shorter, than in the procedures known in the art. An advantage of titanate catalysts is also that the use of fluid is unnecessary and therefore the production process is simpler.

DESCRIPTION OF THE PREFERRED EMBODIMENTS

The production of the products constituting the object of the invention may be further simplified if the propionic acid ester (IV) is produced in a way more closely described below, because then the crude product (IV) obtained as the reaction product can be used as starting material without recrystallization.

It should be noted, however, that propionic acid ester consistent with the chemical formula (IV), whatever the procedure by which it has been produced, is fit to be used for starting material when step (B) is carried out making use of the exchange esterification procedure of the invention.

In view of the invention, it is to be recommended that the propionic acid ester (IV) is produced by an addition reaction between 2,6-dibutylphenol and alkylacrylate (III) using alkali catalysts. Appropriate ones are, in that case, e.g. sodium hydroxide, potassium hydroxide, lithium hydroxide, sodium-boron hydride, lithium-aluminium hydride, sodium and potassium tertiary butoxide, metallic sodium and potassium. 0.5–8% alkali catalyst, preferably 1–5%, calculated on the quantity of 2,6-dibutylphenol, are used.

It is possible in view of the invention that the step (A) is performed either as a molten state reaction or using a solvent for fluid. Solvents which are appropriate are then e.g. dimethylformamide, dimethylacetamide or dimethylsulphoxide, hexamethylphosphamide, acetonitrile, propionitrile or sulphonitrile, sulpholan, dimethylene glycol, tetrahydrofurane or tertiary butylalcohol. Of these, particularly tertiary butylalcohol is well suited to be used in the procedure of the invention. An appropriate quantity of the solvent is 5 parts by weight or less, preferably 0.1–1 parts by weight, of the quantity of 2,6-dibutylphenol.

It is recommendable in view of the invention that the molar proportion of alkylacrylate and 2,6-dibutylphenol in the addition step (A) is in the range 0.7–1.3, preferably 0.8–1.1, the reaction temperature is 60°–130° C., preferably 70°–100° C., and the reaction time is 2–12 h, preferably 6–8 h. All conventional mixing reactors are appropriate for accomplishing the reaction. It is furthermore recommendable in view of the procedure that it can be carried out in a nitrogen atmosphere. Propionic acid ester (IV) thus produced is sufficiently pure to be used as starting material for the purposes of the invention. However, the further use requires that the alkali catalyst is neutralized e.g. with the aid of carboxylic acids or mineral acids and that low-boiling impurities are separated by distilling. The propionic acid ester may then be used in the transesterification reaction without additional purification.

In the procedure of the invention, the exchange esterification step is accomplished using for a catalyst titanic acid esters, particularly tetraalkyl orthotitanates, such as methylethyl, tetramethyl, tetraethyl, n-propyl or isopropyl, n-butyl or isobutyl orthotitanate, or n-butyltitanate polymers. Particularly recommendable in view of the invention is the use as catalyst of tetra-n-butyltitanate. The recommendable quantity of titanate catalyst is 0.1–5%, preferably 0.5–0.3%, of the quantity of propionic acid ester.

In the procedure of the invention, the exchange esterification may be carried out in a fluid or directly in the melt. It is more recommended to carry out the reaction in the melt because hereby the use of extra solvent is avoided and the process is simplified.

When the procedure of the invention is used it is advisable that in the exchange esterification step the molar proportion between propionic acid ester and stearyl alcohol is 0.8–1.5, preferably 0.9–1.2, respectively, the molar proportion between propionic acid ester and thiodiglycol is 1.6–3.0, preferably 1.8–2.2. The recommended reaction temperature is 60°–180° C., preferably 60°–160° C., more preferably 80°–130° C., most preferably 90°–130° C., and the reaction time 1–10 h, preferably 2–6 h. Moreover, it is advisable that during the reaction the low-boiling alcohol which is released in the exchange esterification is removed. In practice, this can be implemented by accomplishing the reaction e.g. at 2–20 mmHg vacuum.

The purification of the products of the invention can be accomplished e.g. by fraction crystallization. Suitable solvents are then hexane, cyclohexane, heptane, ethanol, ispropanol, n-butanol, isobutanol and secondary butanol. Particularly well suited solvents are propylalcohol or butylalcohol either alone or together with a small quantity of water.

The procedure of the invention thus differs from the procedure known in the art in that in the exchange esterification step esters of titanic acid have been used for the catalyst. Hereby, the exchange esterification can be accomplished in considerably shorter time, up to one half of the time required when acid or alkali catalysts of prior art are used. Moreover, less of the coloured impurities are now formed. A considerable advantage of the new catalyst is also that the exchange esterification reaction can with ease be accomplished directly in the melt, without extra solvent fluid, and this makes the process simpler and more economic. If, moreover, the propionic acid ester used in the exchange esterification as starting material is produced in the manner described in the foregoing, the production process is further simplified, since in that case purification of the intermediate product is not absolutely necessary.

In the following, the procedure of the invention is described more in detail with the aid of the following examples.

EXAMPLE 1

Production of 3,5-di-tertiary-butyl-4-hydroxphenyl-methylpropionate 52 ml tertiary butanol, 2.84 g potassium tertiary butoxide, 186.5 g 2,6-di-tertiary butylphenol and 78.0 g methylacrylate were added in a reactor provided with mixing, refluxing system and $N_2$ flushing. The starting materials were allowed to react at 85°–90° C. in an $N_2$ atmosphere, with continuous agitation of the mixture. The product was neutralized with 1.7 ml acetic acid and, finally, vacuum was produced in the equipment for removing the low-boiling impurities. The obtained sample was used as starting material in the exchange esterification step either as such or it was purified by recrystallizing from 95-% isopropanol; yield 206 g (70%), m.p. 64° C.

EXAMPLE 2

Production of stearyl-$\beta$(3,5-dibutyl-4-hydroxphenyl)propionate 5.4 g octadecanol and 6.0 g of the propionic acid ester produced in Example 1 were heated in vacuum at 100° C./50 mmHg for removing moisture, if any, and low-boiling impurities. Thereafter, 0.1 ml tetrabutyltitanate were added for catalyst, and the starting materials were allowed to react for 3 h at 95° C./5 mmHg so that the liberated methanol was distilled off during the reaction. 0.05 ml tetrabutyltitanate were added and the reaction was continued another 30 min. The mixture was dissolved in isopropanol, to which 0.5 ml water was added to decompose the catalyst; yield 8.5 g (80%), m.p. 46°–48° C. The product was recrystallized from 90% isopropanol, m.p. 50°–52° C.

EXAMPLE 3

Production of stearyl-$\beta$(3,5-dibutyl-4-hydroxphenyl)propionate 5.4 g octadecanol and 5.9 g propionic acid ester produced in Example 1, with 0.05 ml tetrabutyltitanate for catalyst, were allowed to react at 105°–110° C./5 mmHg for 2 hrs. The product was recrystallized from 90% isopropanol; yield 8.7 g (82%), m.p. 50°–52° C.

EXAMPLE 4

Production of bis-($\beta$-3,5-dibutyl-4-hydroxybenzyl)-methylcarboxyethyl)sulphide 1.22 g thiodiglycol and 5.9 g propionic acid ester produced in Example 1 were heated at 80°–90° C./7 mmHg for 30 min for removing the moisture, if any, and low-boiling impurities. 0.1 ml tetrabutyltitanate was added as catalyst, and the starting materials were allowed to react for 1 hour at 100° C./7 mmHg so that the methanol that was formed was distilled off. 0.1 ml tetrabutyltitanate were added, and reaction was allowed to react during 3 hrs at 120° C./7 mmHg. 0.35 g thiodiglycol were added, and the reaction was continued for another 30 min. The product was purified by crystallizing it from 90% isopropanol; yield 5.1 g (79%), m.p. 68°–75° C.

EXAMPLE 5

Produciton of bis-($\beta$-(3,5-dibutyl-4-hydroxybenzyl)-methylcarboxyethyl)sulphide 1.3 g thiodiglycol and 5.84 g propionic acid ester produced as in Example 1 were allowed to react in the presence of tetrabutyltitanate (0.05 ml) as catalyst, at 100° C./8 mmHg during 1 h, and further at 120°–130° C./8 mmHg for 1 h. 0.6 ml thiodiglycol and 0.05 ml tetrabutyltitanate were added, and the reaction was continued at 120° C./10 mmHg for 1.5 h. The excess thiodiglycol was distilled off and the product was crystallized from 90% isopropanol; yield 3.3 g (51%), m.p. 68°–75° C.

We claim:

1. Method for producing stearyl-β-(3,5-dibutyl-4-hydroxyphenyl)propionate or bis-(β-3,5-dibutyl-4-hydroxy-benzyl)methylcarboxethyl)sulphide, by transesterification of a propionic acid ester of the formula

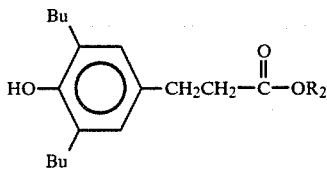

wherein Bu is an n-, secondary, iso- or tertiary butyl group and $R_2$ is an alkyl group containing 1 to 4 carbon atoms, which comprises reacting said propionic acid ester with a stearyl alcohol or thiodiglycol in the presence of a transesterification catalytic effective amount of a titanic acid ester as catalyst in the transesterification, whereby the transesterification reaction is accelerated to form the corresponding propionate or sulphide.

2. The method of claim 1, comprising reacting a molar proportion of said propionic acid ester: said stearyl alcohol about 0.9–1.2, or reacting a molar proportion of said propionic acid ester: said thiodiglycol of about 1.0–2.0.

3. The method of claim 1, comprising carrying out the reaction in the presence of a quantity of said titanic acid ester as catalyst which is about 0.1–5% of a quantity of said propionic acid ester.

4. The method of claim 1, wherein said titanic acid ester is tetra-alkyl orthotitanate.

5. The method of claim 4, wherein said tetra-alkyl orthotitanate is isopropyl or n-butyl titanate.

6. The method of claim 1, wherein the reaction is carried out at a temperature of about 60°–160° C.

7. The method of claim 1, wherein the reaction is carried out over a time of about 1–10 hours.

8. The method of claim 1, wherein said reaction is carried out in a fluid medium, or in the form of a melt without fluid.

9. The method of claim 1, additionally comprising reacting an alkyl acrylate of the formula

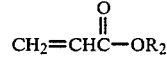

wherein $R_2$ is an alkyl group containing 1 to 4 carbon atoms with 2,6-dibutylphenol in the presence of an alkali catalyst to produce said propionic acid ester, distilling off low boiling impurities and neutralizing said alkali catalyst with of carboxylic acid or mineral acid, and then utilizing said propionic acid ester in said transesterification reaction without additional purification.

10. The method of claim 9, comprising carrying out the reaction for producing said propionic acid ester in the presence of a quantity of said alkali catalyst which is about 1–5% of a quantity of said 2,6-dibutylphenol.

11. The method of claim 10, comprising reacting a molar proportion of said alkyl acrylate: said 2,6-dibutylphenol of about 0.7–1.3.

12. The method of claim 9, wherein the reaction for producing said propionic acid ester is carried out at a temperature of about 70°–100° C. and over a time of about 2–12 hours.

* * * * *